United States Patent [19]

Coates et al.

[11] 4,113,647

[45] Sep. 12, 1978

[54] LIQUID CRYSTALLINE MATERIALS

[75] Inventors: David Coates, Bishops Stortford; George William Gray, Cottingham; Damien Gerard McDonnell, Hull, all of England

[73] Assignee: The Secretary of State for Defence in Her Britannic Majesty's Government of the United Kingdom of Great Britain and Northern Ireland, London, England

[21] Appl. No.: 821,146

[22] Filed: Aug. 2, 1977

[30] Foreign Application Priority Data

Aug. 13, 1976 [GB] United Kingdom .............. 33858/76
Mar. 15, 1977 [GB] United Kingdom .............. 10839/77

[51] Int. Cl.$^2$ .................... G02F 1/13; C09K 3/34; C07C 69/74; C07C 121/62; C07C 121/64
[52] U.S. Cl. .................................. 252/299; 252/408; 260/465 D; 350/350; 560/1; 560/65; 560/66
[58] Field of Search .............................. 252/299, 408; 260/465 D, 473 R; 560/1, 65, 66; 350/350, 160 LC

[56] References Cited

U.S. PATENT DOCUMENTS

| | | | |
|---|---|---|---|
| 3,915,883 | 10/1975 | Van Meter et al. ................. | 252/299 |
| 3,925,237 | 12/1975 | Ross et al. ........................... | 252/299 |
| 3,947,375 | 3/1976 | Gray et al. .......................... | 252/299 |
| 3,951,846 | 4/1976 | Gavrilovic .......................... | 252/299 |
| 3,953,491 | 4/1976 | Steinstrasser et al. ............. | 252/299 |
| 3,974,087 | 8/1976 | Gray et al. .......................... | 252/299 |
| 4,002,670 | 1/1977 | Steinstrasser ..................... | 252/299 |
| 4,013,582 | 3/1977 | Gavrilovic .......................... | 252/299 |
| 4,017,416 | 4/1977 | Inukai et al. ........................ | 252/299 |
| 4,029,595 | 6/1977 | Ross et al. ........................... | 252/299 |
| 4,032,219 | 6/1977 | Constant et al. ................... | 252/299 |

FOREIGN PATENT DOCUMENTS

| | | | |
|---|---|---|---|
| 2,538,865 | 3/1976 | Fed. Rep. of Germany ........... | 252/299 |
| 2,450,088 | 4/1976 | Fed. Rep. of Germany ........... | 252/299 |

OTHER PUBLICATIONS

Dewar, M., et al., J. Am. Chem. Soc., vol. 92, No. 6, pp. 1582–1586 (1970).
Klanderman, B., et al., J. Am. Chem. Soc., vol. 97, No. 6, pp. 1585–1586 (1975).
Coates, D., et al., Mol. Cryst. Liq. Cryst., vol. 31, pp. 275–283 (1975).
Karamysheva, L., et al., Mol. Cryst. Liq. Cryst., vol. 37, pp. 29–34 (1976).

*Primary Examiner*—Benjamin R. Padgett
*Assistant Examiner*—T. S. Gron
*Attorney, Agent, or Firm*—Stevens, Davis, Miller & Mosher

[57] ABSTRACT

Novel liquid crystal materials which are trans-4-alkyl-cyclohexane-1-carboxylic acid esters are provided having the general formula:

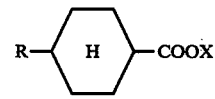

where R is a normal or branched chain alkyl group, which may also contain a chiral center, containing up to ten carbon atoms and X is selected from the groups:

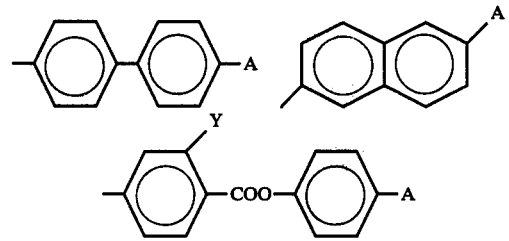

where A is a cyano group, a normal or branched chain alkyl group, which may also contain a chiral center, containing up to ten carbon atoms or an alkoxy group in which the alkyl group is as defined immediately above, and where Y is a halogen, preferably chlorine, or hydrogen.

52 Claims, No Drawings

LIQUID CRYSTALLINE MATERIALS

The present invention is concerned with esters that display liquid crystalline properties.

Liquid crystal phases are exhibited by certain organic compounds and constitute an intermediate phase which exists between the crystalline solid and the fully disordered liquid phase and within which certain long-range ordering of the molecules takes place.

There are two broad types of liquid crystal phase; the smectic mesophase in which the long-range ordering is of a substantially lamellar type and the nematic mesophase in which the ordering is substantially linear, i.e. the molecules tend to line up with the long axes of the molecules parallel. Included sometimes as a sub-class of the nematic mesophase and sometimes classified as a separate mesophase is the cholesteric mesophase. This last type has a helical long-range order superimposed upon the linear order of the nematic mesophase.

In accordance with the present invention a liquid crystal material is a trans-4-alkylcyclohexane-1-carboxylic acid ester having the general formula:

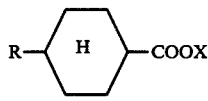
(1)

where R is a normal or branched alkyl group containing up to ten, and preferably up to eight, carbon atoms, which may also contain a chiral center, and X is selected from the groups:

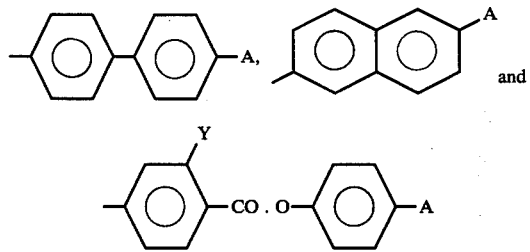

in which A is a cyano group, a normal or branched alkyl group containing up to ten, and preferably up to eight carbons which may also contain a chiral center, or an alkoxy group where the alkyl group therein is as defined immediately above and where Y is a halogen, (preferably chlorine), or hydrogen.

Liquid crystal materials of the present invention have the ability to extend the nematic liquid crystal ranges of other liquid crystal materials without an excessive increase in viscosity which normally occurs when liquid crystal materials are mixed. Substantially all of the cyclohexane esters disclosed above have this property, but the particular properties of individual classes of compounds determine the type of device in which they are best used.

Cyclohexane esters of the present invention in which the group A is a cyano group generally have high positive dielectric anisotropy.

Advantageously such materials have the formula (1) in which R is as defined above and X is selected from

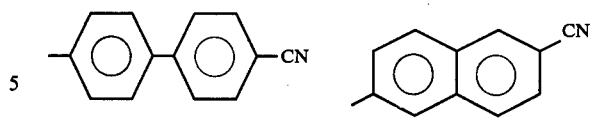

and in accordance with one aspect of the present invention a twisted nematic cell or a phase change cell electro-optic display device includes as its liquid crystal material a cyclohexane ester as defined immediately above or a mixture (solution) of such material in conjunction with other suitable liquid crystal materials. Advantageously a twisted nematic cell incorporates a cyclohexane ester as defined immediately above in conjunction with a low melting nematogen, for example 4-n-heptyl-4-cyanobiphenyl, or other members of that class of cyanobiphenyl.

Cyclohexane diesters of the present invention, that is to say materials having the general formula (1) in which R is as defined above and X is:

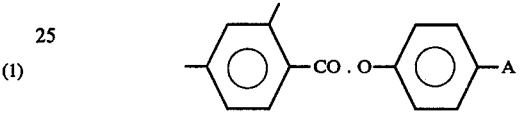

where Y is halogen (preferably chlorine) or hydrogen and A is an alkyl or an alkyloxy group in which the alkyl group is a straight chain, or a branched chain alkyl group containing up to ten, and preferably up to eight carbon atoms generally have relatively little dielectric anisotropy, positive or negative, depending on identity, and in accordance with a second aspect of the present invention a twisted nematic cell or a phase change cell electro-optic desplay device includes as its liquid crystal material a cyclohexane diester as defined immediately above in a mixture (solution) with other suitable liquid crystal materials having relatively high positive dielectric anisotropy. Preferably a twisted nematic cell incorporates a cyclohexane ester or cyclohexane diester as defined above in conjunction with a low melting nematogen for example 4-n-heptyl-4-cyanobiphenyl or other members of that class of alkyl cyano-biphenyl. Furthermore a phase change cell may incorporate a cyclohexane ester or cyclohexane diester as defined above in conjunction with a cholesterogen.

Cyclohexane esters of the present invention in which the group A is alkyl or alkoxy usually have negative dielectric anisotropy. Advantageously such materials, which for the purposes of the present specification are designated cyclohexane monoesters, have the formula (1) in which R is as defined above and X is selected from

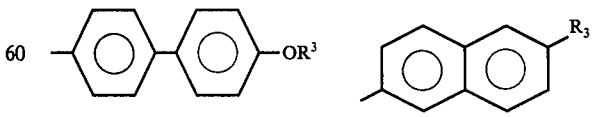

where $R^3$ is a straight chain or branched chain alkyl group containing up to ten, and preferaby up to eight carbon atoms and in accordance with a third aspect of the present invention a dynamic scattering cell or a Freedericksz type cell electro-optic display device includes as its liquid crystal material a cyclohexane monoester as defined immediately above or a mixture (solution) of such material in conjunction with other suitable liquid crystal materials.

When the esters of the present invention contain as R or A a chiral branched alkyl group the liquid crystal phase formed is then cholesteric, and possesses the well known helical molecular arrangement of that phase. The pitch of the cholesteric helix depends upon the nature of the molecule and the position of the chiral centre in it. Such esters have uses as additives in low concentration to nematic mixtures of strong positive dielectric anisotropy to prevent the formation of reversed twist areas in twisted nematic displays. Such esters may also be used in admixture with one another and with other suitable materials which may be chiral and may exhibit a liquid crystalline phase so as to produce a solution (preferably an eutectic) which exhibits a cholesteric phase of suitable pitch length and thermal range to be used in the cholester-nematic phase change type of display.

The present invention will now be described by way of example only with reference to the following Examples, which illustrate methods of preparation of compounds of the present invention and also give physical properties of certain compounds in accordance with the invention.

In the Examples the symbols below indicate the assigned phases:

C — Crystal
$S_A$ — Smectic A
Ch — Cholesteric
N — Nematic
I — Isotropic Liquid
( ) — Brackets around a temperature indicate a monotropic transition not observed during a heating cycle but which appears during cooling.

and phase changes are indicated thus C-$S_A$, crystal to Smectic A, for example. Temperatures are given in ° C.

The compounds of the present invention are prepared by esterification of certain classes of carboxylic acids, phenols and hydroxycarboxylic acids.

EXAMPLE 1

This example describes the preparation of trans-4-alkylcyclohexane-1-carboxylic acids by the following route:

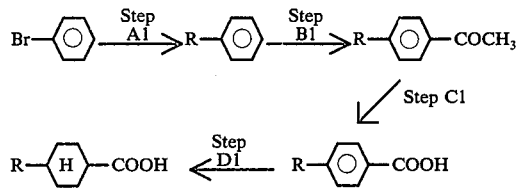

where R is an alkyl group - normal, branched or branched and chiral.

Certain alkylbenzenes, particularly n-alkylbenzenes, are commercially available otherwise they must be prepared from bromobenzene by step A1. The preparation of trans-4-(+)-(2-'methylbutyl)cyclohexane-1-carboxylic acid from bromobenzene by way of (+)-2-methylbutylbenzene will now be described by way of example.

Step A1: The production of (+)-2-methylbutylbenzene.

A solution of bromobenzene (0.51 mole) in sodium dried diethyl/ether (200 ml) is added in drops to magnesium turnings (0.51 g atom) in sodium dried ether (50 ml). A single crystal of iodine is added to initiate the reaction, which is kept going by the addition of the bromobenzene. When addition is complete the solution is heated under reflux for 1 hour.

The solution of the Grignard reagent is then cooled in an ice bath and ferric chloride (0.0025 mole) in ether (2 ml) is added. A solution of (+)-2-methylbutyl bromide (0.54 mole) in sodium dried ether (100 ml) is then added over 30 min. The mixture is left to stir for 48 hours at 25° C. The mixture is then poured into a 20% solution of hydrochloric acid in water, cooled to 0° C. and stirred for 30 min. The product is extracted into ether and the extracts washed with water and dried ($Na_2SO_4$). The ether is evaporated off and the oily residue distilled. The fraction of (+)-2-methylbutylbenzene boiling at 120° C. is collected at a pressure of 15mm of mercury.

Step B1: The production of 4-(+)-(2'-methylbutyl)acetophenone.

Crushed, anhydrous aluminum trichloride (0.295 mole) is suspended in dry carbon disulphide (80 ml). Acetyl chloride (0.25 mole) and (+)-2-methylbutylbenzene (0.23 mole), prepared in Step A1, are dissolved in dry carbon disulphide (80 ml) and added to the suspension of aluminum trichloride under anhydrous conditions. The mixture is then left to stir overnight. The solvent is distilled from the reaction mixture and the viscous residue poured onto crushed ice and stirred for 30 min. The product is extracted into ether, washed with water and dried ($Na_2SO_4$). The ether is removed by rotary evaporation and the oily residue distilled. The product boils at 95° C. at a pressure of 0.1mm of mercury.

Step C1: The production of 4-(+)-(2'-methylbutyl)-benzoic acid.

A solution of sodium hypobromite prepared by dissolving bromine (156g) in a solution of sodium hydroxide (3.5 mole) in water (700 ml) at 0° C. is added to a well stirred solution of 4-(+)-(2'-methylbutyl) acetophenone (0.2 mole), prepared in Step B1, in dioxan (500 ml). Throughout the addition, and for 15 minutes after the addition, the temperature is maintained at 35°–40° C. The excess of sodium hypobromite is destroyed by adding a solution of sodium metabisulphite. Water (3.5 l) is added and bromoform is distilled from the reaction mixture. On cooling the solution is acidified with concentrated hydrochloric acid and the precipitated product is filtered off and washed with water. The product is crystallised from ethanol/water. The m.p. of the colourless crystals is 130° C.

Step D1: The production of trans-4-(+)-(2'-methylbutyl)cyclohexane-1-carboxylic acid A solution of 4-(+)-(2'-methylbutyl)benzoic acid (0.2 mole) in sodium hydroxide (0.205 mole) dissolved in water (160 ml) is hydrogenated in the presence of Raney nickel catalyst (10g) in an autoclave (1 l) at 195° C. and a pressure of hydrogen of 170 atm for 30 hours. On cooling the catalyst is filtered off and the filtrate washed with ether. The aqueous layer is separated and acidified. The precipitated acids are extracted into ether and the ether extracts are washed with water and then dried ($Na_2SO_4$). The ether is distilled off and the acids are dissolved in methanol (200 ml). The solution is treatd successively with 40g and 30g of thiourea. After each treatment with thiourea the crystalline material formed is filtered off. The combined crystallisates are dissolved in a 5% solution (800 ml) of potassium hydroxide in water. This solution is acidified and the 4-trans-(+)-(2'-methylbutyl)cyclohexane-1-carboxylic acid which precipitates out is extracted into ether. The ether extract is washed with water and dried (Na₂SO₄). The ether is evaporated off and the product is crystallised from acetone; the m.p. is 50.3° C.

Other members of this class of carboxylic acid can be prepared by analogous methods, which will be immediately apparent to those skilled in the art.

EXAMPLE 2

Preparation of 6-alkyl-2-naphthols by the following route:

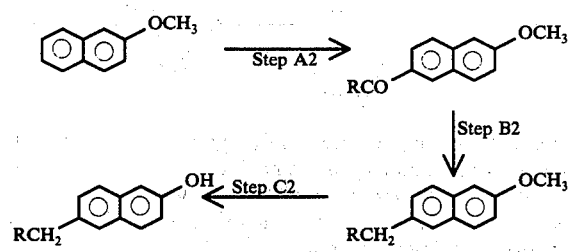

where R is an alkyl group, for example a n-alkyl group.

Step A2: The production of 6-alkanoyl-2-methoxynaphthalenes, by Friedel-Crafts Acylation, may be carried out as follows:

Commercially available 2-methoxynaphthalene (25.8g; 0.15 mole) is added to a cold solution of anhydrous aluminium trichloride (22g; 0.17 mole) in dry nitrobenzene (120 ml). The appropriate alkanoyl chloride RGOG1 (0.17 mole) is added dropwise to the stirred mixture which, when addition is complete, is allowed to stand at room temperature for 48 hours. The dark mixture is then poured onto a mixture of ice, water and concentrated hydrochloric acid and stirred for 0.5 hours. The nitrobenzene layer is separated off and dried over anhydrous magnesium sulphate. The mixture is then distilled under reduced pressure, initially boiling off the nitrobenzene; the required product then distils at about 180°-200° C. at 1mm Hg pressure. The products usually solidify on cooling.

Step B2: The conversion of 6-alkanoyl-2-methoxynaphthalenes to 6-alkyl-2-methoxynaphthalenes may be carried out by the standard synthetic method described by Albrecht, Gustafson and Horgan (J Org Chem 1972 37 3355).

Step C2: Conversion to 6-alkyl-2-naphthols.

A mixture of 6-alkyl-2-methoxynaphthalene (6.5g) in a mixture of constant boiling 46% aqueous hydrobromic acid (24 ml) and a 45% solution of hydrogen bromide in glacial acetic acid (39 ml) is heated under reflux for 24 hours. The solution is cooled, poured into a large volume of water and the 6-alkyl-2-naphthol which precipitates is filtered at the pump. The product is dried and crystallised from a suitable solvent, eg aqueous ethanol.

EXAMPLE 3

Preparation of 6-alkoxy-2-naphthols from commercially available 2,6-dihydroxynaphthalene by the following route:

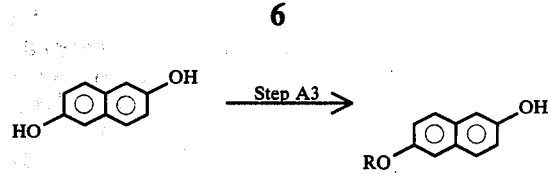

where R is an alkyl group, for example, a n-alkyl group may be carried out by a method analogous to that described for the monoalkylation of p-quinol by Neubert, Carlino, D'Sidocky and Fishel (Liquid Crystals and ordered fluids, Vol 2 (Edited by J. F. Johnson and R. S. Porter) Plenum Press, NY, 1973, p303) but appropriately adapted.

EXAMPLE 4

Preparation of 6-cyano-2-naphthol by the following route:

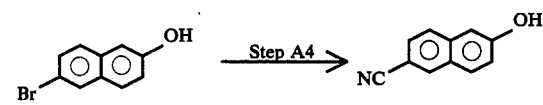

A mixture of commercially available 6-bromo-2-naphthol (12.2g), N-methyl-2-pyrrolidone (23 ml) and copper (I) cyanide is heated under reflux and vigorously stirred for 2 hours. The mixture is protected from atmospheric moisture using CaCl₂ guard tubes. After cooling the mixture is poured into a warm (60° C.) solution of iron (III) chloride in water (200 ml) and concentrated hydrochloric acid (8 ml) and stirred (20 minutes). The cooled mixture is shaken twice with ether (2 × 100 ml) and the combined organic extracts are water washed. Rotary evaporation of the solvent gives a pale brown solid which is crystallised (using decolourising carbon) from a water-ethanol mixture. This yields colourless crystals, m.p. 159°-160° C.

EXAMPLE 5

Preparation of 4'-alkyl-4-hydroxybiphenyls-4-hydroxybiphenyl by the following route:

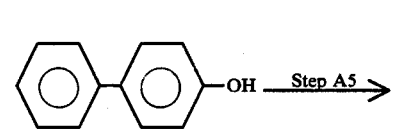

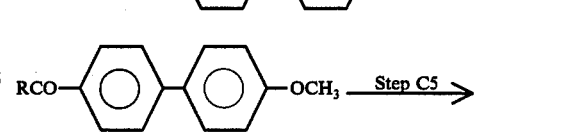

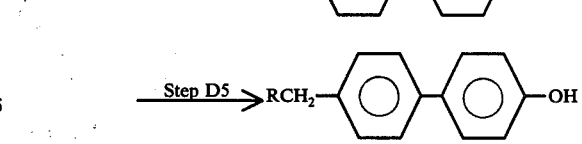

where R is an alkyl group, for example a n-alkyl group.

Step A5: 4-methoxybiphenyl may be prepared by the standard method using dimethyl sulphate described in 'Practical Organic Chemistry' by A. I. Vogel, Longmans Green and Co, London, 3rd edition, p670.

Step B5: The production of 4'-alkanoyl-4-methoxybiphenyls may be carried out by a method analogous to step A2 in Example 2, except that the reaction time is reduced to 24 hours (from 48 hours) and the product is isolated by steam distillation of the nitrobenzene. The solid residue is then crystallised from methanol or ethanol.

Step C5: The conversion of 4'-alkanoyl-4-methoxybiphenyls to 4'-alkyl-4-methoxybiphenyls may be carried out by the standard method described by Albrecht, Gustafson and Horgan (J Org Chem, 1972, 37, 3355) of step B2 in Example 2.

Step D5: The conversion of 4'-alkyl-4-hydroxybiphenyls may be carried out by a method analogous to that in Step C2 of Example 2.

EXAMPLE 6

Preparation of 4'-alkoxy-4-hydroxybiphenyls from commercially available 4,4'-dihydroxybiphenyl by the following route:

where R is an alkyl group, for example a n-alkyl group, may be carried out by a method analogous to that used for the monoalkylation of p-quinol (Neubert, Carlino, D'Sodocky and Fishel, 'Liquid Crystals and Ordered Fluids', vol 2, edited by J. F. Johnson and R. S. Porter, Plenum Press, NY, 1973, p303) but appropriately adapted. The product is crystallised from a solvent such as ethanol and is obtained as colourless crystals. cf Example 3 above.

EXAMPLE 7

Preparation of 4'-cyano-4-hydroxybiphenyl by the following route:

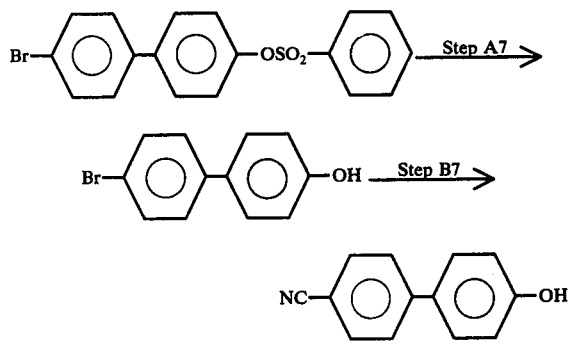

Commercially available 4'-bromo-4-benzenesulphonyloxybiphenyl is hydrolysed with sodium hydroxide by a standard method in a mixture of water and dioxan as solvent. The colourless crystals obtained by crystallisation of the product from ethanol have m.p. 166° C.

Step B7: Conversion to 4'-cyano-4-hydroxybiphenyl may be carried out by a method analogous to Step A4 in Example 4. The product is crystallised from a mixture of water and ethanol. This yields pale tan needles of m.p. 198° C.

EXAMPLE 8

Preparation of certain of the compounds of the present invention require the intermediate production of hydroxyesters of the type

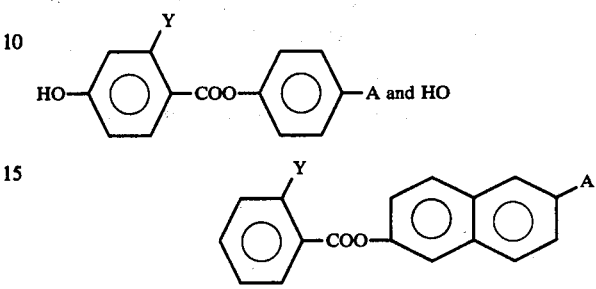

where Y is halogen (preferably chlorine) or hydrogen and A is alkyl, alkoxy or cyano. The general method of preparation of these compounds involves the esterification of 2-chloro-4-hydroxybenzoic acid, or 4-hydroxybenzoic acid with the relevant 4-substituted phenols or 6-substituted 2-naphthols, the preparation of the latter having been described in foregoing Examples 3, 4, 5, 6 and 7.

Of the remaining material required for production of the hydroxyesters described above 4-cyanophenol is commercially available; 2-chloro-4-hydroxybenzoic acid is commercially available; 4-alkylphenols are either commercially available or are prepared by standard methods such as those described by Van der Veen, de Jeu, Grobben and Boven (Mol Cryst Liq Cryst, 1972, 17, 291) for the preparation of 4-alkylanilines, followed by diazotisation of the amines and hydrolysis of the diazonium sulphates; and 4-alkoxyphenols can be prepared by the mono-alkylation of p-quinol using the method of Neubert, Carlino, D'Sidocky and Fishel (Liquid Crystals and Ordered Fluids, vol 2 (Edited by J. F. Johnson and R. S. Porter), Plenum Press, NY, 1973, p303) (cf. Examples 3 and 6 above).

The preparation of 4-n-pentyl-2-chloro-4-hydroxy benzoate by the following route:

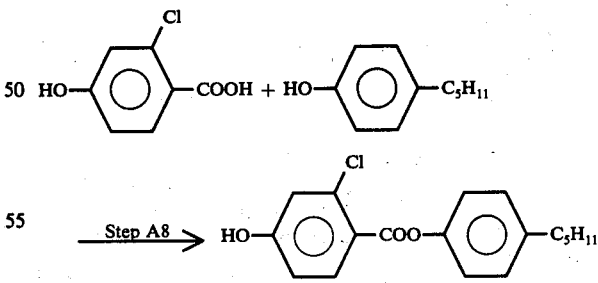

is described as a representative reaction, either of the reactants could be replaced by appropriate equivalents hereinbefore described.

Step A8: The production of 4-n-pentyl 2-chloro-4-hydroxybenzoate is a standard esterification which may be carried out by the method described by Lowrance (Tetrahedron Lett, 1971, 3453) in which the reactants (2-chloro-4-hydroxybenzoic acid and 4-n-pentylphenol in equimolar amounts) are dissolved in toluene and heated in a Dean and Stark apparatus together with sulphuric acid and boric acid as catalysts. After crystallisation from ethanol the m.p. of the product is 150°–151° C.

EXAMPLE 9

Preparation of the liquid crystal esters of the present invention.

Preparation of 6-cyano-2-naphthyl trans-4-n-pentyl-cyclohexane-1-carboxylate by the following route:

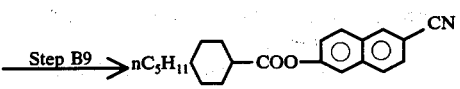

trans-4-n-Pentylcyclohexane-1-carboxylic acid chloride is prepared (step A9) by the standard procedure of heating a solution of trans-4-n-pentylcyclohexane-1-carboxylic acid (0.01 mole) in an excess of thionyl chloride for 2 hours. Removal of the excess of thionyl chloride gives a residue of the acid chloride which is mixed with dry pyridine (40 ml) and cooled to 0°–5° C. 6-Cyano-2-naphthol (0.012 mole), as prepared in Example 4 above, is then added and the solution stirred at room temperature for 20 hours; during this time the reaction mixture is protected from atmospheric moisture by a calcium chloride guard tube. The pyridine is then removed by rotary evaporation. The residual solid is purified by column chromatography on silica gel, using chloroform or chloroform:hexane (2:1) mixture as eluent. The purified ester is isolated and crystallised from hexane or methanol until constant transition temperatures are obtained: crystal-nematic liquid crystal (C-N); 86.5° C.; nematic liquid crystal-isotropic liquid (N-I), 168.3° C.

The foregoing procedure was repeated with the substitution of 4-n-hexyl 2-chloro-4-hydroxybenzoate (prepared in accordance with the description in Example 8) to produce the ester

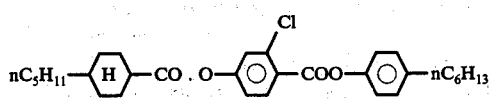

having the following physical properties, G-5, 48° C.; S-N, 53.5° C. N-I, 131° C. (see Table 3 below).

A similar procedure was also carried out using a starting material in Step A9, trans-4-(2-methylbutyl)cyclohexane-1-carboxylic acid (which has chiral centre in alkyl side chain) and with the substitution of 4'-cyano-4-hydroxybiphenyl (as prepared in Example 7) in Step B9 to yield the ester

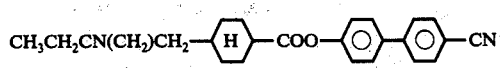

having the physical properties C-$S_A$, 77.6° C.; $S_A$-Ch, 138° C., Ch-I, 190.4° C.

EXAMPLE 10

Further compounds of the present invention were produced by the synthetic methods set forth above and their formulae and physical properties are listed in Tables 1 to 6 below.

TABLE 1

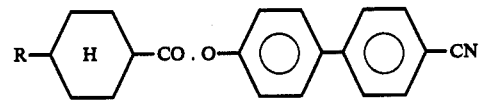

| R | C-$S_A$/N | $S_A$-N | N-I |
|---|---|---|---|
| $CH_3-$ | 102 | — | 213.3 |
| $C_2H_5-$ | 84.4 | — | 229.8 |
| $n-C_3H_7-$ | 94.3 | — | 248.6 |
| $n-C_4H_9-$ | 79.8 | — | 241.9 |
| $n-C_5H_{11}-$ | 85.2 | — | 240.8 |
| $n-C_6H_{13}-$ | 83.6 | 143.2 | 226.7 |
| $n-C_7H_{15}-$ | 91.2 | 179.0 | 227.5 |

TABLE 2

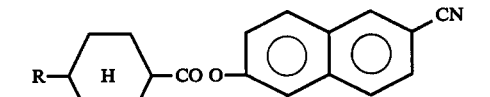

| R | C-$S_A$/N | $S_A$-N | N-I |
|---|---|---|---|
| $CH_3-$ | 113.5 | — | 118.6 |
| $C_2H_5-$ | 76.0 | — | 144.3 |
| $n-C_3H_7-$ | 106.2 | — | 172.6 |
| $n-C_4H_9-$ | 85.0 | — | 166.8 |
| $n-C_5H_{11}-$ | 86.0 | — | 168.0 |
| $n-C_6H_{13}-$ | 72.6 | — | 160.5 |
| $n-C_7H_{15}-$ | 80.0 | 106.0 | 161.0 |

TABLE 3

| $R^1$ | $R^2$ | C-$S_A$/N | $S_A$-N | N-I |
|---|---|---|---|---|
| $C_2H_5-$ | $n-C_3H_7-$ | 45.6 | — | 123.1 |
| $C_2H_5-$ | $n-C_4H_9-$ | 58.3 | — | 112.5 |
| $C_2H_5-$ | $n-C_5H_{11}-$ | 50.5 | — | 116.5 |
| $n-C_3H_7-$ | $n-C_3H_7-$ | 49.0 | — | 144.8 |
| $n-C_3H_7-$ | $n-C_4H_9-$ | 43.2 | — | 134.7 |
| $n-C_3H_7-$ | $n-C_5H_{11}-$ | 52.0 | — | 139.8 |
| $n-C_3H_7-$ | $n-C_6H_{13}-$ | 48.1 | — | 130.7 |
| $n-C_4H_9-$ | $n-C_3H_7-$ | 58.0 | — | 143.0 |
| $n-C_4H_9-$ | $n-C_4H_9-$ | 6.24 | — | 131.9 |
| $n-C_4H_9-$ | $n-C_5H_{11}-$ | 55.0 | — | 134.1 |
| $n-C_4H_9-$ | $n-C_6H_{13}-$ | 56.3 | — | 126.7 |
| $n-C_5H_{11}-$ | $n-C_3H_7-$ | 50.0 | — | 145.2 |
| $n-C_5H_{11}-$ | $n-C_4H_9-$ | 55.2 | (45.0) | 133.2 |
| $n-C_5H_{11}-$ | $n-C_5H_{11}-$ | 52.1 | (30.0 | 136.4 |
| $n-C_5H_{11}-$ | $n-C_6H_{13}-$ | 48 | 53.5 | 131.0 |
| $n-C_6H_{13}-$ | $n-C_6H_{13}-$ | 56.5 | 78.7 | 126.5 |

TABLE 4

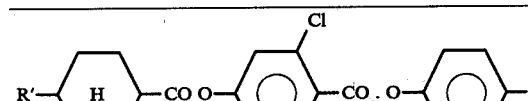

| $R^1$ | $R^2$ | C-N | N-I |
|---|---|---|---|
| $n-C_4H_9-$ | $n-C_4H_9-$ | 51.0 | 163.5 |
| $n-C_4H_9-$ | $n-C_8H_{17}-$ | 58.0 | 146.4 |
| $n-C_5H_{11}-$ | $n-C_5H_{11}-$ | 52.0 | 165.0 |
| $n-C_5H_{11}-$ | $n-C_8H_{17}-$ | 51.0 | 147.8 |

TABLE 5

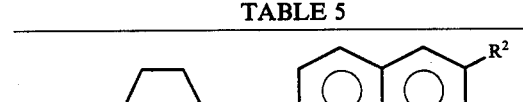

| $R^1$ | $R^2$ | C-$S_A$/N | $S_A$-N | N-I |
|---|---|---|---|---|
| $n-C_4H_9-$ | $n-C_5H_{11}-$ | 66.7 | — | 112.0 |

TABLE 5-continued

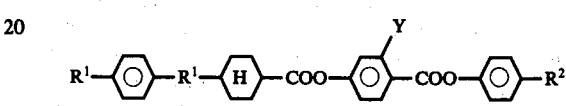

| R$^1$ | R$^2$ | C-S$_A$/N | S$_A$-N | N-I |
|---|---|---|---|---|
| n-C$_5$H$_{11}$— | n-C$_5$H$_{11}$— | 62.0 | (61.2) | 117.6 |
| n-C$_7$H$_{15}$— | n-C$_7$H$_{15}$— | 71.3 | 100.6 | 111.3 |

TABLE 6

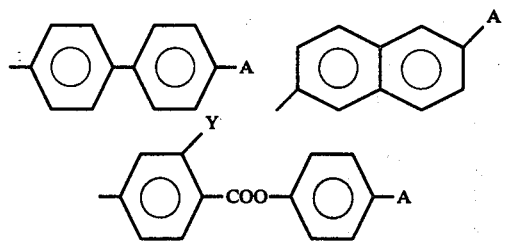

| R$^1$ | R$^2$ | C-N | N-I |
|---|---|---|---|
| n-C$_3$H$_7$— | n-C$_4$H$_9$— | 120.0 | 219.0 |

I claim:

1. A liquid crystal material which comprises a trans-4-alkylcyclohexane-1-carboxylic acid ester having the general formula:

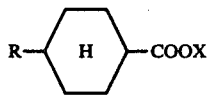

where R is a normal or branched chain alkyl group, which may contain a chiral center containing up to ten carbon atoms, and X is selected from the groups:

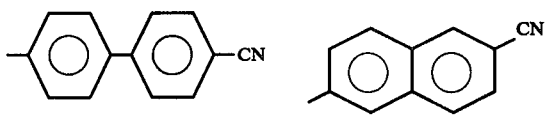

in which A is a cyano group, a normal or branched chain alkyl group, which may also contain a chiral center, containing up to ten carbon atoms, or an alkoxy group in which the alkyl group is as defined immediately above, and where Y is a halogen or hydrogen.

2. A liquid crystal material as claimed in claim 1 and wherein R contains up to eight carbon atoms and the alkyl groups of A contain up to eight carbon atoms.

3. A liquid crystal material as claimed in claim 1 and wherein Y is chlorine.

4. A liquid crystal material as claimed in claim 1 and wherein X is selected from 5. A liquid crystal material as claimed in claim 4 and wherein R is a normal alkyl group containing from one to seven carbon atoms inclusive.

6. A twisted nematic cell or a phase change cell, electro-optic display device containing a liquid crystal material which comprises a cyclohexane ester as claimed in claim 4 or a mixture (solution) of such cyclohexane esters with one another or with other suitably liquid crystal materials.

7. A twisted nematic cell as claimed in claim 6 and wherein the cyclohexane ester is mixed with a low melting nematogen.

8. A twisted nematic cell as claimed in claim 7 and wherein the low melting nematogen is a 4-alkyl-4'-cyanobiphenyl.

9. A twisted nematic cell as claimed in claim 8 and wherein the low melting nematogen is 4-n-heptyl-4'-cyanobiphenyl.

10. A phase change cell as claimed in claim 6 and wherein the cyclohexane ester is used in conjunction with a cholesterogen.

11. A liquid crystal material as claimed in claim 1 and having the formula:

$$R^1-\bigcirc-R^1-\bigcirc H\bigcirc-COO-\bigcirc-COO-\bigcirc-R^2$$

with a Y substituent on the middle ring, where Y is selected from halogen and hydrogen and R$^1$ is selected from normal alkyl group containing up to eight carbon atoms and R$^2$ is selected from normal alkyl groups containing up to eight carbon atoms and normal alkyloxy groups containing up to eight carbon atoms.

12. A liquid crystal material as claimed in claim 11 and wherein Y is chlorine.

13. A liquid crystal material as claimed in claim 12 and wherein R$^1$ contains from two to six carbon atoms inclusive and R$^2$ is a normal alkyl group containing from three to six carbon atoms inclusive.

14. A liquid crystal material as claimed in claim 12 and wherein R$^1$ contains four or five carbon atoms and R$^2$ is a normal alkyloxy group containing from four to eight carbon atoms inclusive.

15. A liquid crystal material as claimed in claim 12 and wherein R$^1$ is ethyl and R$^2$ is n-propyl.

16. A liquid crystal material as claimed in claim 12 and wherein R$^1$ is ethyl and R$^2$ is n-butyl.

17. A liquid crystal material as claimed in claim 12 and wherein R$^1$ is ethyl and R$^2$ is n-heptyl.

18. A liquid crystal material as claimed in claim 12 and wherein R$^1$ is n-propyl and R$^2$ is n-propyl.

19. A liquid crystal material as claimed in claim 12 and wherein R$^1$ is n-propyl and R$^2$ is n-butyl.

20. A liquid crystal material as claimed in claim 12 and wherein R$^1$ is n-propyl and R$^2$ is n-pentyl.

21. A liquid crystal material as claimed in claim 12 and wherein R$^1$ is n-propyl and R$^2$ is n-hexyl.

22. A liquid crystal material as claimed in claim 12 and wherein R$^1$ is n-butyl and R$^2$ is n-propyl.

23. A liquid crystal material as claimed in claim 12 and wherein R$^1$ is n-butyl and R$^2$ is n-butyl.

24. A liquid crystal material as claimed in claim 12 and wherein R$^1$ is n-butyl and R$^2$ is n-pentyl.

25. A liquid crystal material as claimed in claim 12 and wherein R$^1$ is n-butyl and R$^2$ is n-hexyl.

26. A liquid crystal material as claimed in claim 12 and wherein R$^1$ is n-pentyl and R$^2$ is n-propyl.

27. A liquid crystal material as claimed in claim 12 and wherein R$^1$ is n-pentyl and R$^2$ is n-butyl.

28. A liquid crystal material as claimed in claim 12 and wherein R$^1$ is n-pentyl and R$^2$ is n-pentyl.

29. A liquid crystal material as claimed in claim 12 and wherein $R^1$ is n-pentyl and $R^2$ is n-hexyl.

30. A liquid crystal material as claimed in claim 12 and wherein $R^1$ is n-hexyl and $R^2$ is n-hexyl.

31. A liquid crystal material as claimed in claim 12 and wherein $R^1$ is n-butyl and $R^2$ is n-butyloxy.

32. A liquid crystal material as claimed in claim 12 and wherein $R^1$ is n-butyl and $R^2$ is n-octyloxy.

33. A liquid crystal material as claimed in claim 12 and wherein $R^1$ is n-pentyl and $R^2$ is n-pentyloxy.

34. A liquid crystal material as claimed in claim 12 and wherein $R^1$ is n-pentyl and $R^2$ is n-octyloxy.

35. A twisted nematic cell or a phase change cell, electro-optic display device containing a liquid crystal material which comprises a cyclohexane diester as claimed in claim 11 or a mixture (solution) of such cyclohexane diesters with a suitably liquid crystal material having a relatively high positive dielectric anisotropy.

36. A twisted nematic cell as claimed in claim 35 and wherein the cyclohexane diester is mixed with a low melting nematogen.

37. A twisted nematic cell as claimed in claim 36 and wherein the low melting nematogen is a 4-alkyl-4'-cyanobiphenyl.

38. A twisted nematic cell as claimed in claim 36 and wherein the low melting nematogen is 4-n-heptyl-4'-cyanobiphenyl.

39. A phase change cell as claimed in claim 35 and wherein the cyclohexane diester is used in conjunction with a cholesterogen.

40. A liquid crystal material as claimed in claim 1 and wherein X is selected from

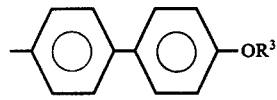 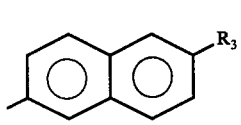

where $R^3$ is a straight chain or branched chain alkyl group containing up to ten carbon atoms.

41. A liquid crystal material as claimed in claim 40 and wherein R and $R^3$ are normal alkyl groups, which may be the same or different, containing up to eight carbon atoms.

42. A liquid crystal material as claimed in claim 40 and wherein R is a normal alkyl group having from three to seven carbon atoms inclusive and $R^3$ is a normal alkyl group having from four to seven carbon atoms inclusive.

43. A liquid crystal material as claimed in claim 40 wherein having the formula:

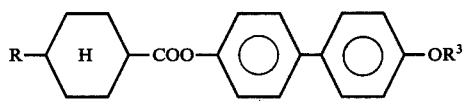

where R is n-propyl and $R^3$ is n-butyl.

44. A liquid crystal material as claimed in claim 40 and having the formula:

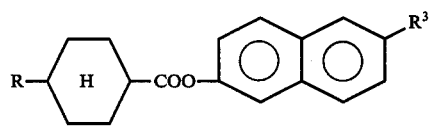

where R is n-butyl and $R^3$ is n-pentyl.

45. A liquid crystal material as claimed in claim 42 and wherein R is n-pentyl and $R^3$ is n-pentyl.

46. A liquid crystal material as claimed in claim 42 and wherein R is n-heptyl and $R^3$ is n-heptyl.

47. A dynamic scattering cell or a Freedericksz type cell, electro-optic display device containing a liquid crystal material which comprises a cyclohexane monoester as claimed in claim 40 or a mixture (solution) of such cyclohexane monoesters with other suitable liquid crystal materials.

48. A liquid crystal material as claimed in claim 1 and wherein any or all of the alkyl groups contain a chiral center.

49. A liquid crystal material as claimed in claim 48 and wherein the alkyl group containing the chiral center is (+)-2-methylbutyl.

50. A liquid crystal material having the formula

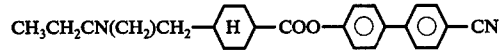

51. A twisted nematic cell which has as its liquid crystal material a nematic mixture of strong positive dielectric anisotropy which includes a low proportion of a liquid crystal material as claimed in claim 48 to prevent the formation of reversed twist areas.

52. A cholesteric-nematic phase change type of display containing a liquid crystal material which comprises a liquid crystal material as claimed in claim 48.

* * * * *